United States Patent [19]

Rantala

[11] Patent Number: 4,850,367
[45] Date of Patent: Jul. 25, 1989

[54] BIOELECTRIC PATIENT MONITOR

[75] Inventor: Börje Rantala, Helsinki, Finland

[73] Assignee: Instrumentarium Corp., Helsinki, Finland

[21] Appl. No.: 25,380

[22] Filed: Mar. 13, 1987

[30] Foreign Application Priority Data

Mar. 17, 1986 [FI] Finland ................... 861093

[51] Int. Cl.$^4$ ................................ A61B 5/02
[52] U.S. Cl. .................................... 128/670
[58] Field of Search ............... 128/670, 671, 709, 700, 128/731, 696, 710

[56] References Cited

U.S. PATENT DOCUMENTS

| | | | |
|---|---|---|---|
| 2,684,278 | 7/1954 | Marchand | 128/710 |
| 3,058,458 | 10/1962 | Daneman | 128/709 |
| 3,465,103 | 9/1969 | Lynch | 128/903 |
| 3,548,806 | 12/1970 | Fisher | 128/671 |
| 3,608,545 | 9/1971 | Novack | 128/700 |
| 4,184,485 | 1/1980 | Agoston | 128/670 |
| 4,243,046 | 1/1981 | Weinstein et al. | 128/709 |
| 4,299,234 | 11/1981 | Epstein et al. | 128/698 |
| 4,331,158 | 5/1982 | Partridge | 128/709 |
| 4,417,592 | 11/1983 | John | 128/731 |
| 4,495,950 | 1/1985 | Schneider | 128/670 |

FOREIGN PATENT DOCUMENTS 0182197 5/1986 European Pat. Off. .

Primary Examiner—Francis Jaworski
Assistant Examiner—George Manuel
Attorney, Agent, or Firm—Quarles & Brady

[57] ABSTRACT

The present apparatus relates to a bioelectric patient monitor, comprising an EKG-amplifier (1) and an EEG-amplifier (2) as well as a patient connecting cable (6), provided with at least five wires with their electrodes (7). The patient connecting cable (6) is connected to amplifiers (1 and 2) by way of a distributor switch (4). By selecting with distributor switch (4), it is possible to monitor either a 5-wire electrocardiogram or optionally a 3-wire electrocardiogram and electroencephalogram.

11 Claims, 2 Drawing Sheets

OPTION A

OPTION B

BIOELECTRIC PATIENT MONITOR

The present invention relates to a bioelectric patient monitor, comprising an EKG-amplifier and an EEG-amplifier as well as a patient connecting cable, having at least wires with their electrodes. An object of the invention is to provide a combined EKG- and EEG-monitor for combining, in an easy-to-operate manner, the possibilities of monitoring with a single patient connecting cable either a 5-wire EKG (electrocardiogram) or both a more usual 3-wire EKG and EEG (electroencephalogram).

BACKGROUND OF THE INVENTION

The most usual way of monitoring EKG is a so-called 3-wire connection. In some cases, however, e.g. when cardiac ischemia is suspected, it is desireable to use a 5-wire measuring connection. On the other hand, the EEG-monitoring especially during a surgical operation has been found a good measuring variable, which correlates with the depth of anaesthesia and warns the brain of a threatening lack of oxygen. However, the EEG-monitoring has been generally considered troublesome; partly due to difficulties encountered in the interpretation of EEG but partly also due to the complexity, high price and bulkiness of an EEG-apparatus and the extra trouble caused by electrode connections.

SUMMARY OF THE INVENTION

In order to achieve the above object of the invention, a patient monitor of the invention is characterized in that EKG- and EEG-aplifiers are connected to a distributor switch, by way of which a patient connecting cable can be connected to amplifiers in a manner that, by selecting with the distributor switch, it is possible to monitor either a 5-wire electrocardiogram or optionally a 3-wire electrocardiogram and electroencephalogram. Thus, the invention offers a possibility of utilizing the two often unused electrode lines of a 5-wire EKG-cable for simple EEG monitoring.

DESCRIPTION OF THE DRAWINGS

The invention will now be described in more detail with reference made to the accompanying drawing, which shows a general block diagram for a monitor of the invention as well as optional (A and B) applications of a patient connecting cable.

DESCRIPTION OF THE ILLUSTRATED EMBODIMENT

Figure 1:
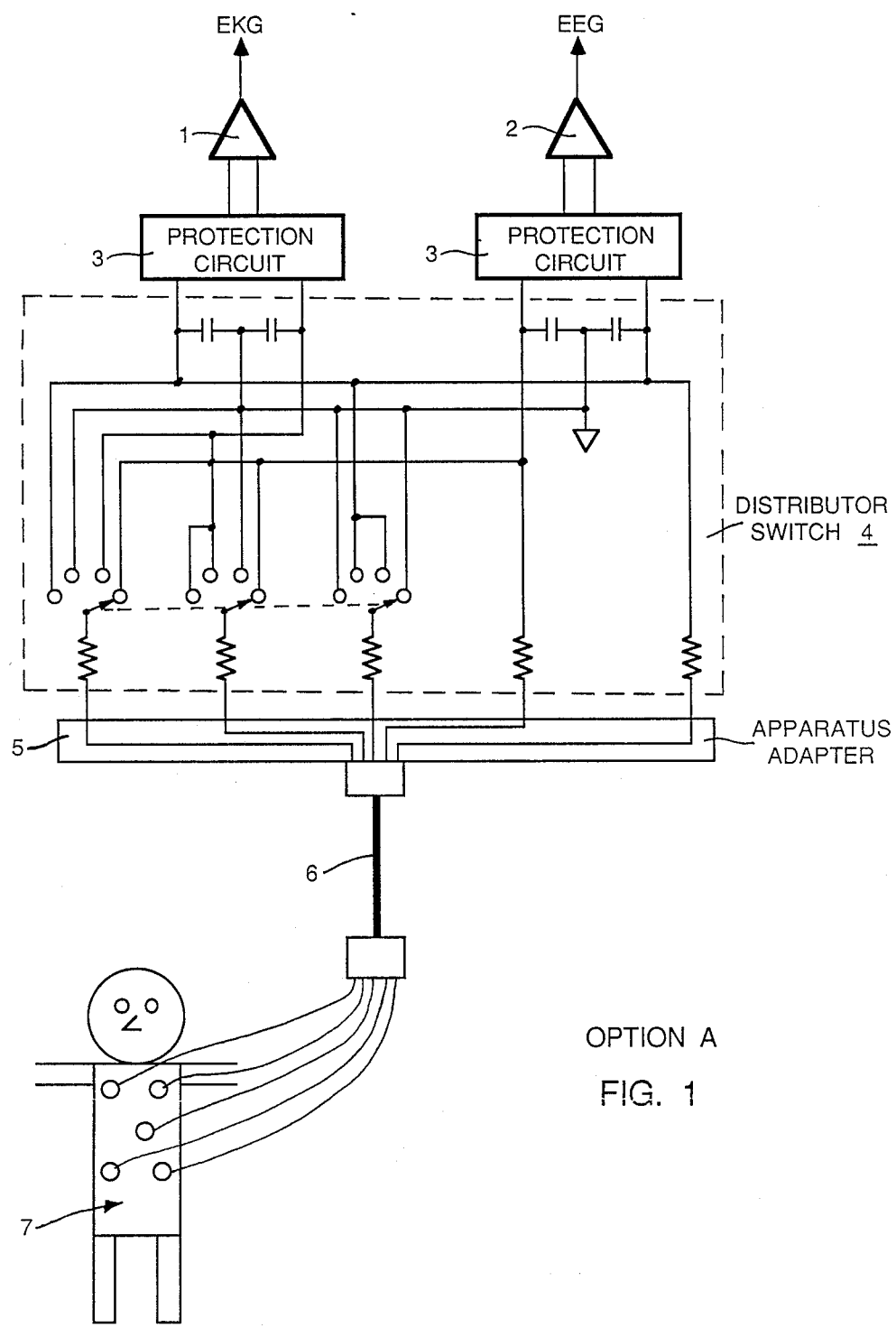
Figure 2:
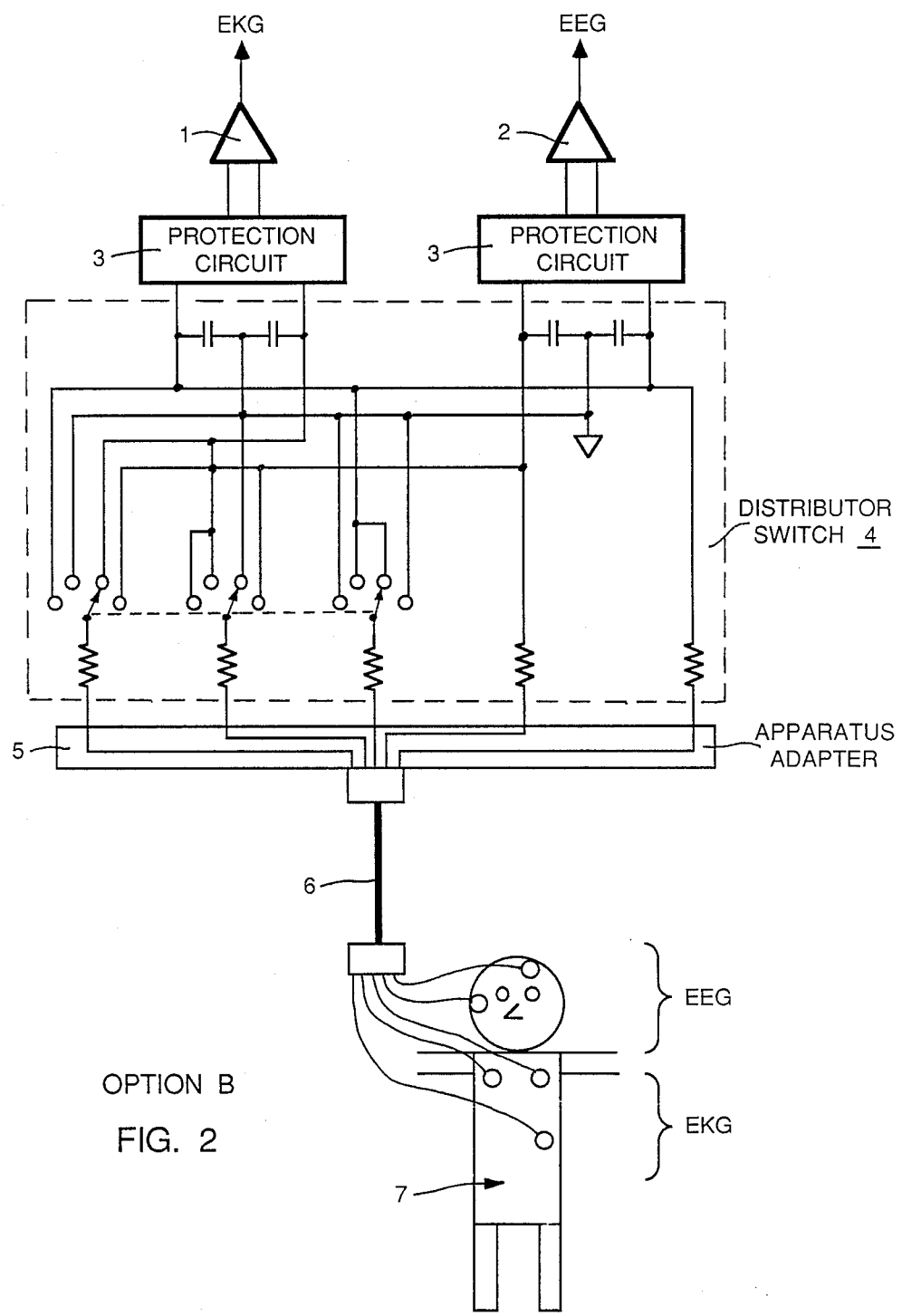

The figure illustrates preamplifiers 1 (EKG) AND 2 (EEG) of a combined EKG-EEG-amplifier. Thus, the amplifier always includes both EKG- and EEG-components. Preamplifiers 1 and 2 are connected by way of protection circuits 3 to a distributor switch 4, which may be mechanical or electrical.

A 5-wire patient connecting cable 6 can be connected by way of an apparatus adapter 5 to distributor switch 4. Cable 6 is provided with five electrodes 7 which in option A are connected to a patient for monitoring a 5-wire EKG and in option B the function of this monitor is the simultaneous monitoring of a 3-wire EKG and a 2-wire EEG. The shift from one function to the other between options A and B is effected not only by setting electrodes 7 at the spots required by the measuring operation but also by selecting the corresponding mode of operation or function with distributor switch 4 in order to connect proper electrode wires to appropriate amplifiers 1 and 2. It should be noted that the EEG-channel uses a so-called reference electrode of the EKG-channel for saving one wire of the normal minimum configuration (3 wires) of an EEG-monitor. In addition to or instead of an electroencephalogram, one of the amplifiers of a monitor along with its associated electrodes can be adapted to monitor the electric muscular activity or electromyogram of the head area.

I claim:

1. In a bioelectric patient monitor, an input circuit comprising:
    a first amplifier for a first physiological activity monitoring device consisting of an electrocardiograph;
    a second amplifier for a second physiological activity monitoring device;
    five electrodes for attaching to a patient to be monitored;
    an electrical cable having five wires each of which connected to a different one of said five electrodes; and
    a distributor switch having a first state in which said switch couples the five wires of the electrical cable to said first amplifier, and having a second state in which said switch couples three of the wires of said electrical cable to said first amplifier and the other two wires of said electrical cable to said second amplifier.

2. The input circuit as recited in claim 1 wherein the second physiological activity is an electroencephalograph.

3. The input circuit as recited in claim 1 wherein the second physiological activity monitoring device is an electromyograph.

4. The input circuit as recited in claim 1 wherein the monitor is configured as a five wire electrocardiograph when the distributor switch is in the first state.

5. The input circuit as recited in claim 4 wherein the monitor is configured as a three wire electrocardiograph and an electromyograph when the distributor switch is in the second state.

6. The input circuit as recited in claim 4 wherein the monitor is configured as a three wire electrocardiograph and an electroencephalograph when the distributor switch is in the second state.

7. The input circuit as recited in claim 6 wherein the first amplifier receives electrocardiograph signals over the three wires simultaneously with the second amplifier receiving electroencephalograph signals over the two remaining wires when the distributor switch is in the second state.

8. An input circuit for a bioelectric patient monitor comprising:
    a first amplifier for a first physiological activity monitoring device consisting of an electrocardiograph;
    a second amplifier for a second physiological activity monitoring device;
    five electrodes for attaching to a patient to be monitored; and means for coupling said electrodes to said first and second amplifiers, having a first state in which the five electrodes are coupled to provide electrocardiograph input signals to said first amplifier, and having a second state in which three of the electrodes are coupled to provide electrocardiograph input signals to said first amplifier and the other two electrodes are coupled to provide signals for the second physiological activity to said second amplifier.

9. The input circuit as recited in claim 8 wherein the input circuit configures the monitor as a three electrode electrocardiograph and an electroencephalograph when said means for coupling is in the second state.

10. The input circuit as recited in claim 9 wherein the first amplifier receives electrocardiograph signals from the three electrodes simultaneously with the second amplifier receiving electroencephalograph signals from the two remaining electrodes when said means for coupling is in the second state.

11. The input circuit as recited in claim 8 wherein the input circuit configures the monitor as a three electrode electrocardiograph and an electromyograph when said means for coupling is in the second state.

* * * * *

UNITED STATES PATENT AND TRADEMARK OFFICE
CERTIFICATE OF CORRECTION

PATENT NO. : 4,850,367
DATED : July 25, 1989
INVENTOR(S) : Borje Rantala

It is certified that error appears in the above-identified patent and that said Letters Patent is hereby corrected as shown below:

In column 1, line 35, change "aplifiers" to --amplifiers--.

In column 2, line 36, after "activity" insert --monitoring device--.

Signed and Sealed this

Fifteenth Day of May, 1990

*Attest:*

HARRY F. MANBECK, JR.

*Attesting Officer*        *Commissioner of Patents and Trademarks*